(12) United States Patent
Nakanishi

(10) Patent No.: US 11,872,178 B2
(45) Date of Patent: Jan. 16, 2024

(54) FACIAL LIGAMENT/FACIAL FASCIA RELEASE DEVICE

(71) Applicant: UNISH INC., Osaka (JP)

(72) Inventor: Hirofumi Nakanishi, Osaka (JP)

(73) Assignee: UNISH INC., Osaka (JP)

( * ) Notice: Subject to any disclaimer, the term of this patent is extended or adjusted under 35 U.S.C. 154(b) by 0 days.

(21) Appl. No.: 18/002,588

(22) PCT Filed: May 18, 2021

(86) PCT No.: PCT/JP2021/018847
§ 371 (c)(1),
(2) Date: Dec. 20, 2022

(87) PCT Pub. No.: WO2022/180868
PCT Pub. Date: Sep. 1, 2022

(65) Prior Publication Data
US 2023/0190572 A1 Jun. 22, 2023

(30) Foreign Application Priority Data
Feb. 26, 2021 (JP) .................................. 2021-030528

(51) Int. Cl.
*A61H 15/00* (2006.01)
*A61H 7/00* (2006.01)

(52) U.S. Cl.
CPC ............. *A61H 15/00* (2013.01); *A61H 7/008* (2013.01); *A61H 2015/0014* (2013.01); *A61H 2201/10* (2013.01)

(58) Field of Classification Search
CPC .. A61H 15/00; A61H 7/00; A61H 2015/0007; A61H 7/008;
(Continued)

(56) References Cited

U.S. PATENT DOCUMENTS

| 3,297,024 A | 1/1967 | Robinson |
| 6,090,055 A | 7/2000 | Frajdenrajch |

(Continued)

FOREIGN PATENT DOCUMENTS

| CN | 205252317 U | 5/2016 |
| ES | 2552230 T3 | 11/2015 |

(Continued)

OTHER PUBLICATIONS

WIPO, Japanese International Search Authority, International Search Report (with English translation) dated Jul. 13, 2021 in International Patent Application No. PCT/JP2021/018847, 6 pages.

(Continued)

*Primary Examiner* — Gary Jackson
*Assistant Examiner* — Sebastian X Lukjan
(74) *Attorney, Agent, or Firm* — MASUVALLEY & PARTNERS; Peter Martinez

(57) ABSTRACT

Provided is a device useful for facial beauty treatment by efficiently releasing ligaments, SMAS fascia, and the like, and having a compact structure with multiple functions and an ease for a user to use at home.

The present invention provides a device (1) that has a massage function by rolling of a roller (3), a suction function by a suction portion (4), and a stimulation function by outputting a stimulation signal by a conductive element (34) fixed to a bottom surface (23) or a roller (3), and can efficiently and reliably implement an effect such as releasing the ligaments such as a facial skin of a user. In addition, since a circumferential protrusion (61) is formed on the peripheral edge of an opening portion (24) for performing suction so as to surround the opening portion (24), it is possible to enhance confidentiality during suction by the suction portion (4), and the effect described above can be (Continued)

efficiently exhibited. And the device (1) has multiple functions and a compact structure, which is easy for the user to use even at home.

6 Claims, 5 Drawing Sheets

(58) Field of Classification Search
CPC ........ A61H 2015/0014; A61H 2201/10; A61H 15/0092; A61H 9/005; A61H 2205/022; A61B 18/12; A61N 1/36; A61N 1/06
See application file for complete search history.

(56) References Cited

U.S. PATENT DOCUMENTS

| | | | |
|---|---|---|---|
| 6,585,667 B1* | 7/2003 | Muller | A61H 7/008 |
| | | | 601/6 |
| 10,675,211 B2* | 6/2020 | Nakanishi | A61H 23/02 |
| 10,888,491 B2 | 6/2021 | Aghion | |
| 2007/0191745 A1* | 8/2007 | Tucker | A61H 7/003 |
| | | | 601/135 |
| 2008/0221504 A1* | 9/2008 | Aghion | A61N 1/40 |
| | | | 604/20 |
| 2016/0128605 A1* | 5/2016 | Moreno | A61H 7/008 |
| | | | 601/6 |
| 2018/0161233 A1 | 6/2018 | Nakanishi | |
| 2019/0192873 A1* | 6/2019 | Schwarz | A61F 7/00 |

FOREIGN PATENT DOCUMENTS

| | | | |
|---|---|---|---|
| JP | 2004-073812 A | | 3/2004 |
| JP | 2005-296042 A | | 10/2005 |
| JP | 3158360 U | | 3/2010 |
| JP | 2011-045610 A | | 3/2011 |
| JP | 2015-163179 A | | 9/2015 |
| JP | 2016016030 A | | 2/2016 |
| KR | 2015010075 A | * | 1/2015 |
| WO | 2017/038822 A1 | | 3/2017 |

OTHER PUBLICATIONS

WIPO, Japanese International Search Authority, Written Opinion (with English translation) dated Jul. 13, 2021 in International Patent Application No. PCT/JP2021/018847, 11 pages.

WIPO, Japanese International Search Authority, Notification of Transmittal of International Preliminary Report on Patentability (with English translation) dated Apr. 5, 2022 in International Patent Application No. PCT/JP2021/018847, 3 pages.

WIPO, Japanese International Search Authority, International Preliminary Report on Patentability (with English translation) dated Apr. 5, 2022 in International Patent Application No. PCT/JP2021/018847, 10 pages.

European Patent Office, extended European search report dated Oct. 24, 2023 for European application No. 21927071.7, 9 pages.

* cited by examiner

FACIAL LIGAMENT/FACIAL FASCIA RELEASE DEVICE

RELATED APPLICATIONS

This application is the U.S. National Phase of and claims priority to International Patent Application No. PCT/JP2021/018847, International Filing Date May 18, 2021; which claims benefit of Japanese Patent Application No. 2021-030528 filed Feb. 26, 2021; both of which are incorporated herein by reference in their entireties.

TECHNICAL FIELD

The present invention relates to a facial ligament/facial fascia release device. More specifically, the present invention relates to a facial ligament/facial fascia release device useful for releasing the facial ligament, an SMAS fascia (corresponding to facial fascia), and the like.

BACKGROUND ART

A device such as a beauty device or a facial treatment device is brought into contact with a face such as a cheek to approach not only facial skin (skin) but also facial muscles and bring the skin to a more beautiful state. By using such a device, it is possible to easily perform skin treatment or the like at home without requiring specialized treatment or care at an aesthetic salon, a clinic, or the like.

Furthermore, periodically going to an aesthetic salon or the like tends to be a burden both in terms of schedule and money, and additionally, in recent corona pandemic, it is difficult to go out. Therefore, skin treatments and the like using devices such as beauty devices and facial treatment devices are widely performed at home than before.

As the devices such as beauty devices or facial treatment device used in a self-treatment or self-care, for example, a device of a type that performs massage of a user's face by rotating a roller or a sphere for massage while pressing a roller or a sphere against the user's face or the like is known (for example, see Patent Literature 1, Patent Literature 2, and the like).

In a device such as a beauty roller having such a configuration, a user rotates a massage roller portion while pressing the massage roller portion against the face of the user in a state where the user holds a grip portion to massage the face of the user.

CITATION LIST

Patent Literature

Patent Literature 1: JP 2015-163179 A
Patent Literature 2: JP 3158360 Y

SUMMARY OF INVENTION

Technical Problem

In recent years, it has been said that the release of ligaments is effective for face beauty. Here, the "ligament" is a membrane tissue existing in the face, and is also called a facial ligament that is constituted by a thin string-like fiber tissue like a seashell.

In general, there are five types of ligaments (facial ligaments): parotid gland ligaments, suborbital ligaments, cheekbone ligaments, occlusal muscle ligaments, and mandibular ligaments, and these ligaments have a role of connecting and supporting the facial skin (skin), facial expression muscles, or fat to bones. As described above, the ligaments are considered to be an important tissue that supports the facial skin, fat, and the like, prevents falling, and suppresses facial sagging.

The ligaments deteriorate and become hard and thin due to various factors such as aging, stress, lifestyle, which may make it impossible to support the facial skin (skin) and the fat. The deterioration of the ligaments is related to the facial sagging, and it is also said that the deterioration of the ligaments causes an aged face such as the sagging of lower half of the face and formation of a nasolabial fold. On the other hand, when such ligaments can be trained in a well-balanced manner and released (loosened), it is considered that the facial skin and muscles are drawn, leading to a lift-up (a face lift-up), and an effect of rejuvenating the face and creating a small face can be obtained.

In addition, the superficial musculo-aponeurotic system (SMAS) fascia (superficial fascia: also called smas musculus), which can be said to be a base that supports the skin (the skin), is a fascia that can be called a fascia of the face (a facial fascia) that firmly connects the muscles of face surface and the facial expression muscles to the bones and directly acts on the ligaments (the facial ligaments) supporting the fat. On the other hand, when the SMAS fascia is weakened, wrinkles in a forehead, outer corners of eyes, and parts between eyebrows and the sagging of cheeks are increased in the same manner as the ligaments are deteriorated, and the nasolabial fold is deepened, causing an aging face.

It is not an overstatement that tensions of the facial skin, facial expression muscles, and the like is maintained by such ligaments and SMAS fascia. On the other hand, since more than half of muscles in the face cannot be moved by themselves, it is said that approaching to move depth of the muscles in normal massage, exercise, and the like is difficult, and this is the same in the massage using only the roller disclosed in Patent Literature 1 and the like.

On the other hand, a device for forcibly moving a ligament or the like by applying a weak current to a muscle using an electrical stimulation signal such as an electrical muscle stimulation (EMS) to treat the face or the like has also been studied. Such device that emits a stimulation signal such as EMS is effective for releasing ligaments, peeling adhesion of SMAS fascia (release of SMAS fascial), and the like. However, such device often has only one function or has a large volume, and it has been desired to provide a device with multiple functions and a compact structure.

The present invention has been made in view of the above problems, and an object of the present invention is to provide a device that is useful for facial beauty by efficiently releasing ligaments, SMAS fascia, and the like, and has a multiple functions and a compact structure that is easy for a user to employ even at home.

Solution to Problem

In order to solve the above problem, a device according to the present invention
is a device applicable to a human face, the device including:
a main body portion including, on an outer surface, an insertion portion having a space into which a hand of a user can be inserted, and a placement portion on which a palm of the hand of the user inserted into the insertion portion can be placed;

a roller disposed inside an opening portion formed in a bottom surface of the main body portion and capable of outputting a stimulation signal;

a conductive element fixedly disposed inside the opening portion and capable of outputting a stimulation signal; and a suction portion configured to be built in the main body portion, pneumatically communicate with the opening portion, and suck external air from the opening portion, wherein a bank-like continuous circumferential protrusion is formed on a peripheral edge of the opening portion so as to surround the opening portion.

In the present invention described above, the device according to the present invention is characterized in that the roller disposed in the opening portion enters inside the opening portion.

In the present invention described above, the device according to the present invention is characterized in that the roller and the conductive element are attached inside a roller cup, the roller cup is disposed on a bottom surface of the main body portion, the opening portion formed on the bottom surface is an opening portion of the roller cup, and the circumferential protrusion is a peripheral edge of the opening portion of the roller cup.

In the present invention described above, the device according to the present invention is characterized in that, the stimulation signal is at least one selected from a group consisting of electrical muscle stimulation (EMS) and radio frequency (RF).

In the present invention described above, the device according to the present invention is characterized in that, a side of the main body portion into which a hand of the user is inserted has a bill shape in a side view in which the insertion portion is formed between an upper beak portion and a lower beak portion, the placement portion serves as an upper surface of the lower beak portion, and the main portion is formed with a finger insertion portion that communicates with the insertion portion and includes an opening hole into which a finger of a user can be inserted.

In the present invention described above, the device according to the present invention is characterized in that a lower surface of the upper beak portion and an upper surface of the lower beak portion have a rounded shape protruding upward.

Advantageous Effects of Invention

A device of the present invention has a massage function by rotating a roller disposed in the main body portion, a suction function by the suction portion, and a stimulation function (an electrical stimulation function by application of a stimulation signal (an electrical signal)) by outputting a stimulation signal from the conductive element fixed to the bottom surface or the roller, and can be implemented by combining all these functions at the time of use. Therefore, it is possible to efficiently and reliably implement release of ligaments and SMAS fascia of the facial skin or the like of the user, and it is possible to efficiently implement facial beauty such as facial treatment or care. In addition, according to the present invention, it is possible to easily perform the so-called fascia release for efficiently peeling adhesion of fascia of the facial skin of the user, elimination of cellulite, and the like.

Furthermore, since the bank-like continuous circumferential protrusion is formed on the peripheral edge of the opening portion that performs suction so as to surround the opening portion, it is possible to enhance confidentiality during suction by the suction portion, it is possible to reliably suck hard and loose facial skin into the opening portion, it is possible to appropriately hold the facial skin that is a target region, and it is possible to efficiently exhibit the effect described above.

Furthermore, as described above, the device has a compact structure in which the main body portion is integrated by disposing the suction portion inside and the fixed conductive element or roller capable of outputting the stimulation signal on the bottom surface while being with multiple functions, and includes the insertion portion formed of the space into which the hand of the user can be inserted, and the placement portion on which the palm of the hand of the user inserted into the insertion portion can be placed on the outer surface, and can be used by being gripped with one hand, and thus the device is easy for the user to use even at home.

DESCRIPTION OF EMBODIMENTS (I) Configuration of Device 1 According to the Present Invention Hereinafter, one aspect of the device 1 according to the present invention will be described with reference to the drawings.

Figure 1:
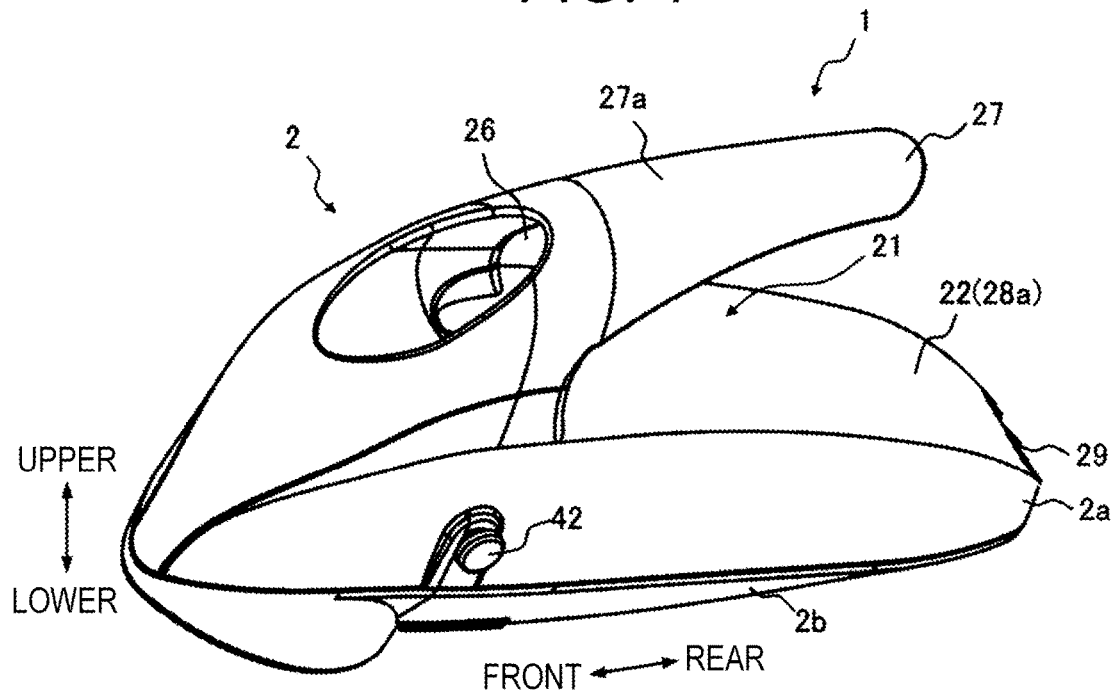
FIG. 1 is a perspective view illustrating one aspect of a device according to the present invention as viewed from above.
Figure 2:
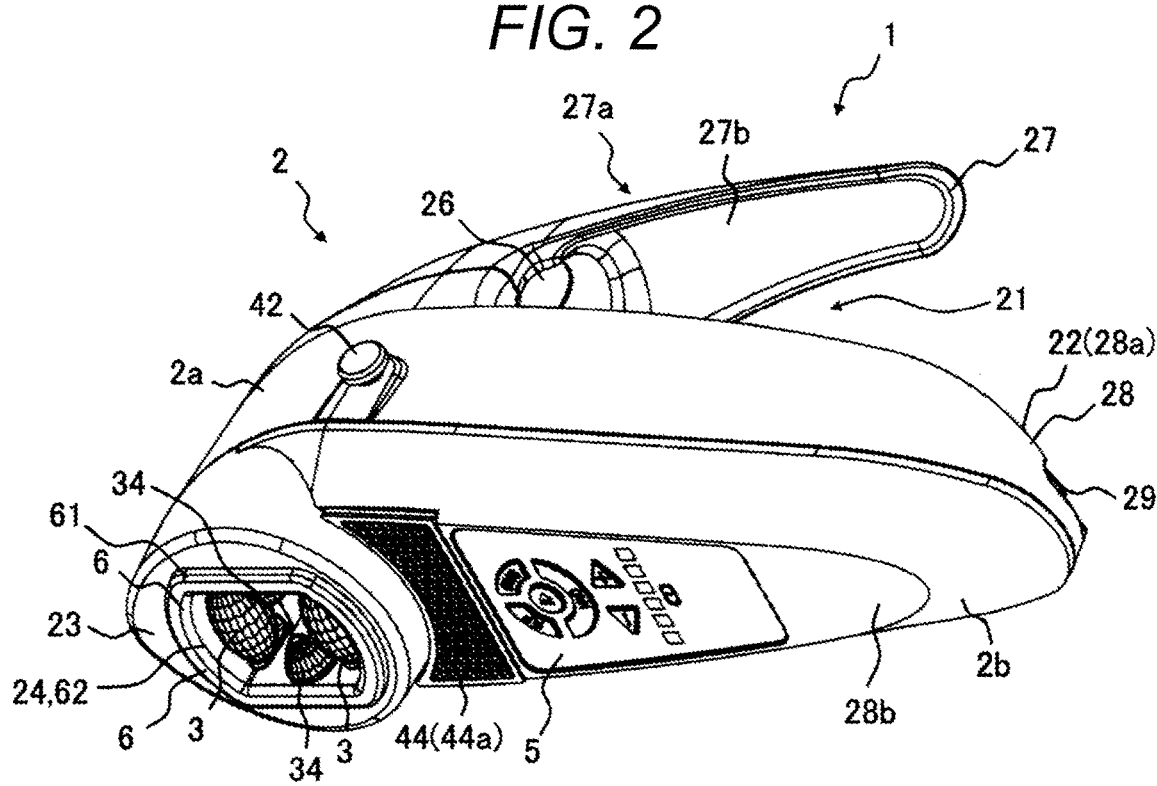
FIG. 2 is a perspective view illustrating one aspect of the device according to the present invention as viewed from below.
Figure 3:
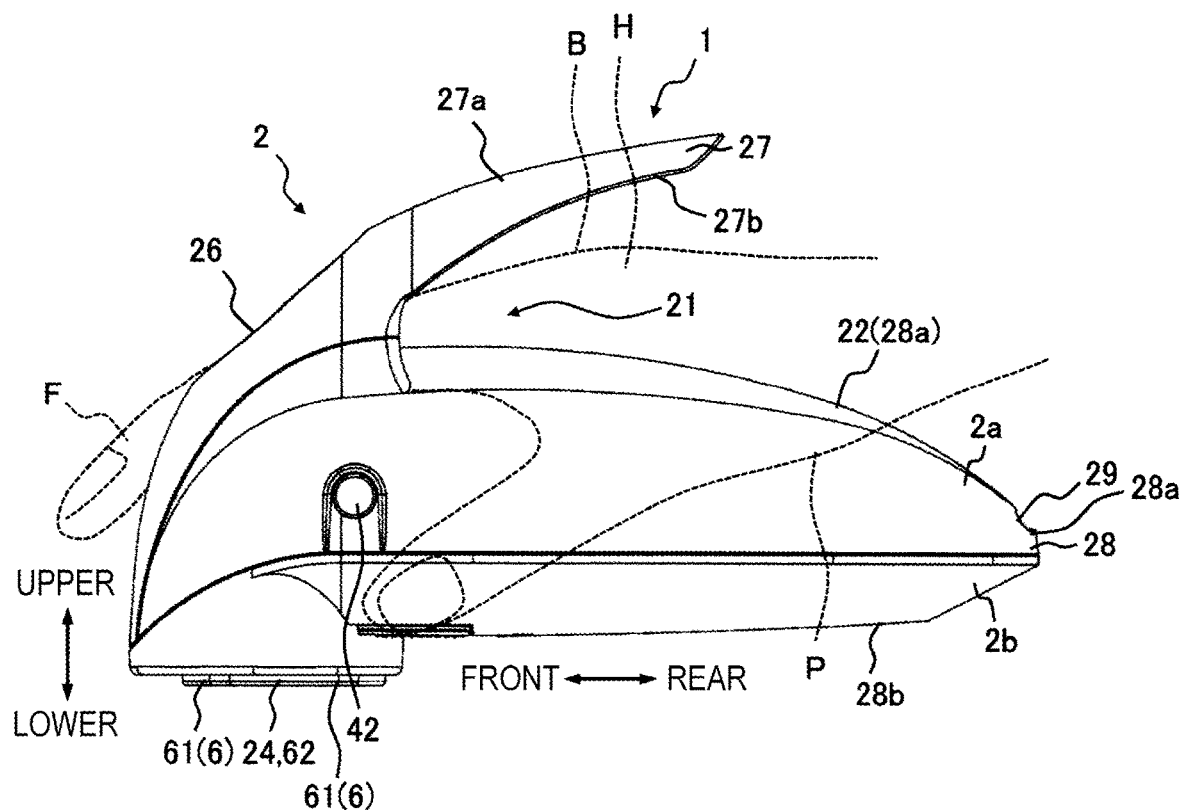
FIG. 3 is a side view of the device.
Figure 4:
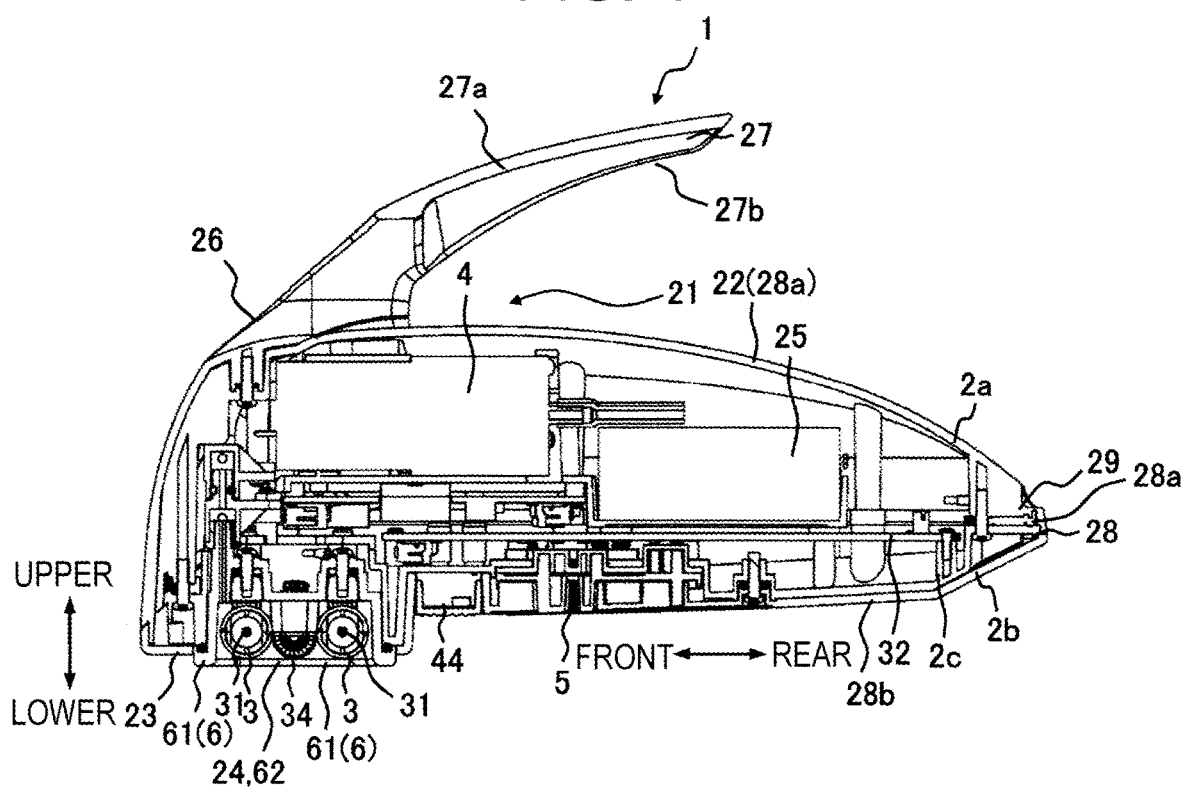
FIG. 4 is a schematic view of an internal structure of the device.

FIG. 1 is a perspective view illustrating one aspect of the device 1 according to the present invention as viewed from above, FIG. 2 is a perspective view illustrating one aspect of the device 1 according to the present invention as viewed from below, FIG. 3 is a side view of the device 1, and FIG. 4 is a schematic view of the internal structure of the device 1. Here, directions such as "upward" and "downward", "forward" and "rearward" in the present invention are as shown together with arrows in FIG. 1 and the like.

(Configuration, Shape, and the Like of Device 1)

The device 1 according to the present invention is applicable to a human face, and includes, as a basic configuration, an insertion portion 21 consisting of a space into which a hand H of a user can be inserted, a main body portion 2 including, on an outer surface, a placement portion 22 on which a palm P of the hand of the user inserted into the insertion portion 21 can be placed, a roller 3 disposed inside an opening portion 24 formed on a bottom surface 23 of the main body portion 2 and capable of outputting a stimulation signal, a conductive element 34 disposed while being fixed inside the opening portion 24 and capable of outputting a stimulation signal, and a suction portion (a pump) 4 configured to be built in the main body portion 2, pneumatically communicating with the opening portion 24, and sucking external air from the opening portion 24.

Furthermore, in FIG. 3, the hand H of the user holding the device 1 is indicated by a dotted line, and the hand H and the palm P of the hand are described with reference to FIG. 3. In addition, FIG. 4 does not illustrate a part of a member incorporated in the main body portion 2 of the device 1.

The main body portion 2 of the device 1 of the present invention that can be used as a beauty device, a facial treatment device, or the like incorporates components and members such as the pump 4 that is a suction portion mounted on a component mounting portion 2c (see FIG. 4), and the conductive element 34, a roller 3, and the like are disposed in the opening portion 24 of the bottom surface 23. The main body portion 2 of the device 1 can be made of, for example, a synthetic resin such as an ABS resin.

In the present embodiment, as shown in FIGS. 1 to 4, an aspect is shown in which a side of the main body portion 2 formed by combining a main body upper portion 2a and a main body lower portion 2b into which the hand H of the user is inserted (a side on which the insertion portion 21 is formed, which is a rear (see an arrow direction in FIG. 1, the same applies hereinafter) side of the main body portion 2 in FIG. 1 and the like) has a beak shape in the side view, and a side opposite to the side into which the hand H of the user is inserted (in FIG. 1 and the like, a front side of the main body portion 2 (see the arrow direction in FIG. 1, the same applies hereinafter)) has a streamline shape connected from the bottom surface 23.

As illustrated in FIG. 1 and the like, the bill shape refers to a state in which a bird opens a bill, and an opened portion of the bill serves as the insertion portion 21. As to be described later, an upper beak portion 27 exists above the opened portion and a lower beak portion 28 exists below the opened portion.

Furthermore, the bill shape in the side view can be said to be an L-shape in which an L-shaped vertical line is oblique and forms an acute angle with an L-shaped horizontal line. The L-shaped vertical line corresponds to the upper beak portion 27, an L-shaped horizontal line corresponds to the lower beak portion 28, and an empty portion of two L-shaped lines corresponds to the insertion portion 21.

The bill shape of the main body portion 2 is configured such that the upper beak portion 27 and the lower beak portion 28 having a rounded and pointed tip are formed, and the insertion portion 21 is formed between the upper beak portion 27 and the lower beak portion 28. The upper beak portion 27 is connected to a streamline shape in front of the main body portion 2. In the present embodiment, both an upper surface 27a and a lower surface 27b are formed in a rounded shape protruding upward, an upper surface 28a of the lower beak portion is formed in a rounded shape protruding upward, and the placement portion 22 on which the palm P of the hand of the user can be placed when the hand H of the user is inserted into the insertion portion 21 formed between the upper beak portion 27 and the lower beak portion 28.

In the device 1 according to the present embodiment, the main body portion 2 is a device 1 having multiple functions in which the pump 4 is disposed inside and the conductive element 34 fixed to the roller 3 capable of outputting the stimulation signal is compactly integrated with the bottom surface 23, and the device 1 has a shape that can be held and used with one hand by the configuration described above.

In the present embodiment, a substantially elliptical finger insertion portion 26 that communicates with the insertion portion 21 and includes one opening hole into which a finger F of the user can be inserted is formed on a front side of the main body portion 2. With this configuration, the user can insert the hand H into the insertion portion 21 and use the finger F inserted into the finger insertion portion 26. Furthermore, when the hand H of the user is inserted, the lower surface 27b of the upper beak portion, which is a portion in contact with the back of a hand B and the palm P, and the upper surface 28a of the lower beak portion to be the placement portion 22 have a rounded shape protruding upward, so that the back of the hand B and the palm P to be inserted easily fit.

Furthermore, as illustrated in FIGS. 1 to 4, in the bill shape, when the upper beak portion 27 is shorter (in the present embodiment, an aspect is shown in which the upper beak portion 27 has a length of about half of that of the lower beak portion 28 in the side view) than the lower beak portion 28 in the side view, the back of the hand B can be more easily fitted together with the palm P of the hand H of the user. As described above, the main body portion 2 illustrated in the present embodiment has a shape having an ergonomic design in consideration of ease of use.

When using the device 1 configured by the main body portion 2 having such a shape, for example, the user may insert the hand H into the opened insertion portion 21, place the palm P on the placement portion 22 of the lower beak portion 28, insert the finger (for example, an index finger or the like) F into the finger insertion portion 26, grip the device 1 with one hand, and use the roller 3 arranged in the opening portion 24 on the front side of the bottom surface 23 in a state of being in contact with the facial skin or the like. In addition, the upper beak portion 27 may be grasped with the hand H for use.

(Operation Panel 5)

Figure 5:
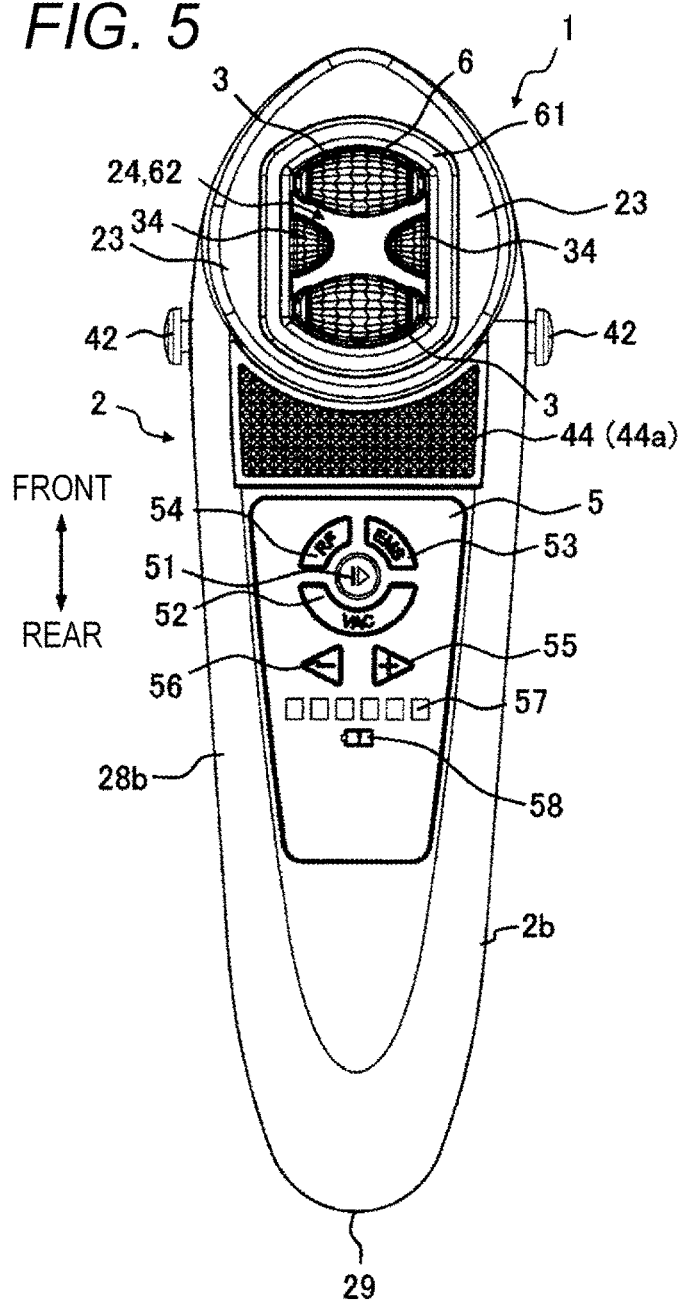
FIG. 5 is a bottom view of the device.

As illustrated in FIG. 2 and FIG. 5 to be described later, an operation panel 5 is disposed on a lower surface 28b of the lower beak portion. The operation panel 5 disposed on the lower surface 28b of the lower beak portion operates power on/off, a stimulation function of the roller 3 and the conductive element 34 to be described later, the suction function of sucking external air using the opening portion 24 as a suction port, and the like.

Figure 6:
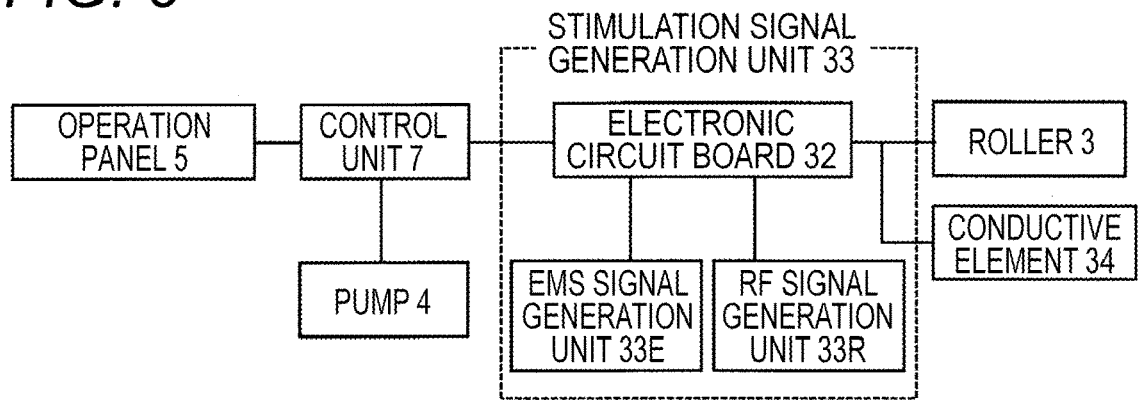
FIG. 6 is an explanatory view illustrating an outline of control by an operation panel.

FIG. 5 is a bottom view of the device 1. Furthermore, FIG. 6 is an explanatory view illustrating an outline of control by the operation panel 5. As the outline of control is illustrated in FIG. 6, the operation panel 5 illustrated in FIG. 5 is electrically connected to the roller 3 and the fixed conductive element connected to a stimulation signal generation unit 33 including an electronic circuit board (electric circuit board) 32 (see FIG. 4) provided with an ultrasonic oscillation circuit not illustrated and the pump 4 via a control unit 7 incorporated in the main body portion 2 of the device 1, and enables selection of these modes, operation of output level, and the like. As illustrated in FIG. 6, the stimulation signal generation unit 33 includes an EMS signal generation unit 33E and an RF signal generation unit 33R, and is connected to an electronic circuit board 32.

As illustrated in FIG. 5, in the operation panel 5, a power button 51, a suction mode button 52, an EMS mode button 53, an RF mode button 54, a level raising button 55, and a level lowering button 56 are formed as operation buttons, and a level display lamp 57 and a battery lamp 58 are formed as lamps.

Furthermore, the operation panel 5 includes an EMS mode and an RF mode that are modes of a stimulation function (an electrical stimulation function by application of a stimulation signal (an electrical signal)), and an EMS mode button 53 is formed as a button for operating the EMS mode, and an RF mode button 54 is formed as a button for operating the RF mode. The modes of the stimulation function are also described as the EMS mode and the RF mode.

The power button 51 operates turning on/off (on (ON)/off (OFF)) of a power supply of the device 1, and start, stop, pause, and the like of a suction mode, an EMS mode, and an RF mode. For example, when the power button 51 is pressed for several seconds, the power supply may be turned "on", and the lamp of the suction mode button 52, the EMS mode button 53, and the lamp of the RF mode button 54 may blink.

In a case where the operation by the device 1 is temporarily stopped, for example, the operation may be temporarily stopped while the suction mode or the EMS mode (the RF mode) is kept at a level that is being used by pressing the power button 51 during operation. Furthermore, the power supply may be turned "off" by pressing the power button 51 for several seconds.

Moreover, the operation in the suction mode can be started by pressing the power button 51 again in a state where the power is turned "on". However, the suction mode button 52 may be converted into the suction mode (the suction function can be operated) by being pressed when an operation state is the EMS mode (the EMS function can be operated) or the RF mode (an RF function can be operated). Conversely, the EMS mode button 53 may be converted into the EMS mode by being pressed when the operation state is in the suction mode. Similarly, the RF mode button 54 may be converted into the RF mode by being pressed when the operation state is in the suction mode.

In addition, the EMS mode and the RF mode may be applied at the same time without any problem. However, the EMS mode and the RF mode may not be applied at the same time because frequency bands are different and it is not necessary to apply the EMS mode and the RF mode at the same time. Note that details of the EMS and the RF (RF wave) that are electrical stimulation signals will be described later.

The level raising button 55 increases the output of operating modes (the suction mode, the EMS mode, and the RF mode), and for example, the output of the mode is increased by one step every time the button is pressed once. The level lowering button 56 lowers the output of the operating modes (the suction mode, the EMS mode, and the RF mode), and for example, the output of the mode is lowered by one step every time the button is pressed once.

The level display lamp 57 displays levels of the suction mode, the EMS mode, and the RF mode according to the state of the operation described above, and the levels are displayed in six stages in FIG. 6. Furthermore, the battery lamp 58 displays a remaining amount of a built-in battery (a rechargeable battery) 25 (see FIG. 4), and can display, for example, a remaining amount of the battery of 30% or more (there is no problem in use) when turned off, a remaining amount of the battery of less than 30% (which is about time to recharge) when turned on, a remaining amount of the battery of less than 10% (which needs to be recharged immediately) when blinking, and the like. Furthermore, the 30% and 10% described above can be arbitrarily determined.

The battery (rechargeable battery) 25 incorporated in the main body portion 2 of the device 1 can be easily recharged, for example, by connecting a charging terminal of a charger (not illustrated) to an insertion port 29 disposed outside the device 1. The insertion port 29 may be formed at an arbitrary position (for example, the front side of the main body portion 2, and the like) of the device 1 in accordance with the shape of the charger.

(Roller 3 and Conductive Element 34)

Figure 7:
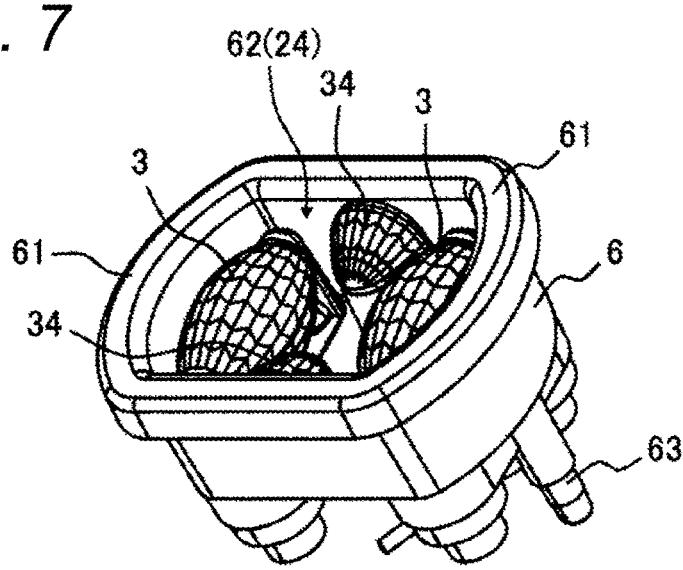
FIG. 7 is a perspective view illustrating a roller cup.
Figure 8:
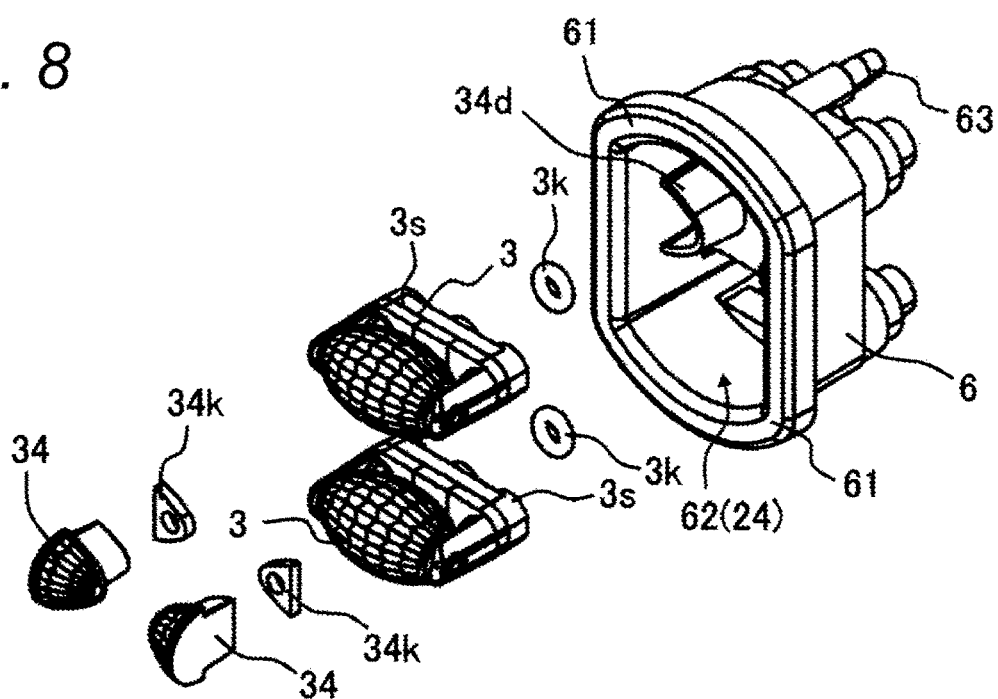
FIG. 8 is an exploded perspective view illustrating a roller, a conductive element, and a roller cup.
Figure 9:
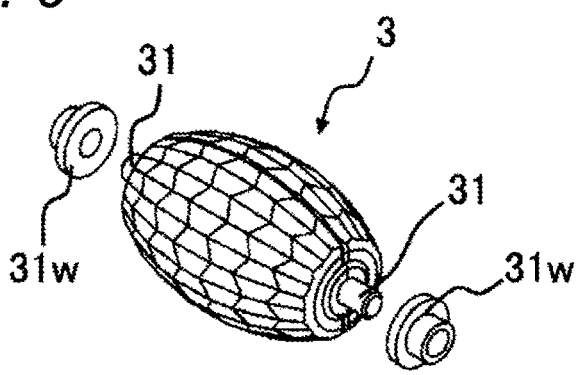
FIG. 9 is a perspective view illustrating the roller.

FIG. 7 is a perspective view illustrating the roller cup 6, FIG. 8 is an exploded perspective view illustrating the roller 3, the conductive element 34, and the roller cup 6, and FIG. 9 is a perspective view illustrating the roller 3. In the device 1 of the present embodiment, the roller 3 and the conductive element 34 can be integrated, and a signal such as EMS or RF can be output in a state where the facial skin is sucked and sandwiched.

As also illustrated in FIG. 5, the opening portion 24 is formed in the bottom surface 23 of the main body portion 2 of the device 1. In the present embodiment, the opening portion 24 has a substantially rectangular shape in which a short side is a curve bulging outward, and as illustrated in FIG. 5 and the like, the roller cup 6 illustrated in FIG. 7 is attached to the opening portion 24, and an opening portion 62 of the roller cup 6 directly becomes the opening portion 24 of the device 1 (the main body portion 2). In the opening portion 62 (the opening portion 24) of the roller cup, a cup suction path 63 connected to a suction hole (not illustrated) formed inside and the suction portion (the pump) 4 to be described later are pneumatically communicated, so that the opening portions 62 and 24 are pneumatically communicated with the suction portion (the pump) 4, and the suction portion 4 sucks external air from the opening portions 62 and 24.

Considering that the device 1 of the present invention can be applied to the face, the areas of the opening portions 24 and 62 are preferably 600 to 1000 $mm^2$, and particularly preferably 750 to 850 $mm^2$, for example.

Furthermore, a bank-like continuous circumferential protrusion 61 is formed on a peripheral edge of the opening portion 24 (in the present embodiment, the opening portion 62 of the roller cup) of the bottom surface 23 so as to surround the opening portions 24 and 62 (a circumferential frame (a frame portion) surrounding the opening portion 62 is formed). Since the circumferential protrusion 61 is formed, it is possible to increase confidentiality during suction by the suction portion (the pump) 4, and it is possible to reliably suck hard and loose facial skin (skin) into the opening portion 24 (in the present embodiment, it refers to the inside of the opening portion 62 of the roller cup 6), and it is possible to appropriately hold the facial skin, which is a part to be cosmetically treated.

Furthermore, in the present embodiment, the roller cup illustrated in FIG. 7 is disposed on the bottom surface 23 of the main body portion 2, and the opening portion 62 of the roller cup 6 directly becomes the opening portion 24 of the device 1 (the main body portion 2). Therefore, the circumferential protrusion 61 is formed by the peripheral edge of the opening portion 62 of the roller cup 6 appearing on the bottom surface 23 of the main body portion 2. The shape of the roller cup 6 is not particularly limited as long as the roller cup 6 can be disposed on the bottom surface 23, and the roller cup 6 has a shape in which the roller 3 and the conductive element 34 are attached inside. For example, the roller cup 6 can have any shape having an opening such as a bottomed cylindrical shape (which corresponds to the opening portion 62 of the roller cup 6), a bowl shape, or the like.

A height of the circumferential protrusion 61 may be appropriately determined according to the size of the device 1 or the like, but is preferably approximately 1 to 6 mm as viewed from the bottom surface 23 of the device 1. When the height of the circumferential protrusion 61 is within such a range, it is possible to reliably maintain confidentiality. The height of the circumferential protrusion 61 is particularly preferably 2 to 4 mm as viewed from the bottom surface 23 of the device 1. Moreover, since a top of the circumferential protrusion 61 is in contact with the facial skin, the top of the circumferential protrusion 61 preferably has a flat shape with rounded corners as illustrated in FIG. 3 and the like.

Furthermore, two rollers 3 and two conductive elements 34 are disposed inside the opening portion 62 of the roller cup 6. It is preferable that the roller 3 disposed inside the roller cup 6 enters inside the opening portion 62 (which is common to the opening portion 24).

At the time of suction by the suction portion (the pump) 4, the facial skin is drawn into the opening portions 24 and 62. However, since the roller 3 enters the inner side of the opening portions 24 and 62, the facial skin drawn into the opening portions 24 and 62 can be reliably rolled. In addition, conversely, when the face skin is rolled by the roller, the face skin applied to the inside of the opening portions 24 and 62 is easily drawn, and suction can be performed in such a drawn state. The roller 3 preferably enters approximately 0.5 to 3 mm inward when viewed from the opening portions 24 and 62 (the top of the circumferential protrusion 61), and particularly preferably enters 1 to 2 mm inward.

As described above, since the device 1 of the present invention is disposed in a state where the roller 3 relatively enters the inside when viewed from the opening portion 24, a member such as the roller 3 disposed inside the opening portions 24 and 62 does not appear outside.

A rotation shaft 31 (see FIG. 9) of the roller (the rotor) 3 is disposed so as to be orthogonal to an operation direction (see a front-rear arrow directions in FIG. 1) of the device 1, and in the present embodiment, an aspect is shown in which the roller (the rotor) 3 is formed of a member having a substantially egg shape (a substantially entire spindle shape with a large diameter at a central portion) having an uneven surface with a surface pleat shape.

The roller 3 is mounted inside the opening portion 24 so as to be rotatable about the rotation shaft 31 supported so as to be orthogonal to the operation direction of the device 1, and two (a pair of) rollers 3 are supported in a state of being arranged in parallel. As also shown in FIGS. 7 to 9, the roller 3 disposed inside the opening portions 24 and 62 is configured such that the rotation shaft 31 is attached to an attachment base 3s (see FIG. 8) via a washer 31w so as to be rotatable about the rotation shaft 31. Furthermore, the attachment base 3s is attached to the roller cup 6 via an interposing member 3k (see FIG. 8). Number of the rollers 3 may be one or more, but is preferably two or more. The interval between two or more rollers 3 is not particularly limited, but is preferably 16 to 30 mm.

In the roller 3 rotatably (in a rotatable way) supported by the rotation shaft 31, the hand H of the user grips the main body portion 2 and presses the bottom surface 23 on which the roller 3 is disposed against the skin of the user or the like, whereby an outer peripheral portion of the roller 3 is pressed against the body by disposing against the skin or the like. Furthermore, by moving the roller 3 in the operation direction of the device 1 described above, the roller 3 rotates and rolls to massage the facial skin and the like, which is useful for the release of ligaments and the like. In addition, since the rolling of the roller 3 can pull up the facial skin and the like, it is easy to eliminate cellulite and the like by the suction function.

Note that the device 1 of the present invention is effective for release of ligaments and SMAS fascia (corresponding to facial fascia) of the facial skin (skin), and is also useful for the so-called fascia release, elimination of cellulite, and the like. Hereinafter, these effects may be collectively referred to as "release of ligament or the like".

In the present embodiment, the conductive element 34 has a shape obtained by cutting the roller 3 described above along a plane orthogonal to the rotation shaft 31 and further along a plane passing through the rotation shaft 31. In the present embodiment, the conductive element 34 is fixedly attached (fitted) onto a support 34d inside the roller cup 6 via the interposing member 34k so as to be located on the left and right between the rollers 3 with respect to the two rollers 3 arranged side by side.

The conductive element 34 fixedly disposed inside the opening portions 24 and 62 serves as an electrode, and generates a stimulation signal, so that an electrical stimulation function (some are simply referred to as "stimulation function") by application of the stimulation signal (the electrical signal) is effective for release of ligaments, and the like. The number of conductive elements 34 may be one or more, but is preferably two or more.

As a representative example of the stimulation function, for example, an electrical muscle stimulation (EMS) function or a radio frequency (RF, also called an RF wave) function is known, and the stimulation signal according to the present invention is preferably selected from the EMS or RF functions. Furthermore, the stimulation function is preferably used in combination with the suction function effective for the release of ligaments or the like. Note that, in the present invention, there are also places referred to simply as the "EMS function" and places referred to simply as the "EMS", and there are also places referred to simply as the "RF wave" and places referred to simply as the "RF (wave) function", which are referred to as "RF" simply.

Furthermore, similarly to the conductive element 34, the roller 3 disposed in the opening portion 24 serves as an electrode, can generate a stimulation signal, and can perform the electrical stimulation by application of a stimulation signal (an electrical signal). In the present invention, since two types of electrodes (elements) such as the roller 3 and the conductive element 34 can emit stimulation signals, an electrical stimulation signal is efficiently applied, and a cosmetic effect corresponding to the electrical stimulation signal can be expected.

The EMS function and the RF function cause electricity to flow to a human to stimulate cells and muscles. In the device 1, the roller 3 and the conductive element 34 come into contact with the skin or the like to apply a stimulation signal (a low frequency or high frequency stimulation signal) to the skin to be contacted or the like, and the roller 3 and the conductive element 34 simultaneously stimulate the skin with the EMS or the RF, so that it is possible to efficiently perform the release of ligaments by being used in combination with the suction function.

The device 1 uses the roller 3 as a medium that exhibits not only a massage function by rolling but also a stimulation function of generating a stimulation signal using the roller 3 as an electrode. Furthermore, in that the massage function and the stimulation function can be performed in combination with the suction function using the suction portion (the pump) 4 effective for the release of ligaments, the effect of release of ligaments can be synergistically exhibited.

The stimulation signal applies a low to high frequency electrical stimulation signal (including low frequency pulse, medium frequency pulse, high frequency pulse, and the like) in order to efficiently exhibit an electrical stimulation function by application of a stimulation signal (an electrical signal). For example, in a case where the EMS signal (EMS) is used as the electrical stimulation signal, it is considered that the stimulation signal may be selected and used from a frequency range of a low frequency (for example, 1 to 1000 Hz or the like), a medium frequency (for example, 1000 to 2000 Hz or the like), or a high frequency (for example, it is set to 3000 Hz or more, 3000 to 50000 Hz, and the like).

In particular, in a case where an RF signal (an RF wave) is used as the electrical stimulation signal, for example, it is considered that the stimulation signal may be selected and used from a frequency range such as a high frequency (for example, 10000 to 1000000 Hz or the like).

In general, as the frequency is higher, the stimulation can be applied to a deep place such as the facial skin. For example, the lower frequency is several millimeters (mm) below the facial skin (the skin), and the medium frequency is several centimeters. In addition, at a high frequency, a stimulation reaching a so-called inner muscle can be given at a depth of 10 cm or more. As described above, the type and frequency range of the electrical stimulation signal may be determined in consideration of how deep the stimulation is given to the facial skin or the like.

As illustrated in FIG. 6, the stimulation signal generation unit 33 to which the conductive element 34 and the roller 3 are electrically connected is provided with the ultrasonic oscillation circuit (not illustrated), includes the electronic circuit board 32 including the EMS signal generation unit 32E and the RF signal generation unit 32R, and can apply a stimulation signal using the conductive element 34 and the roller 3 as a generation source based on a signal from the ultrasonic oscillation circuit including adjustment of an output level by an operation from the operation panel 5 via the control unit 7.

Furthermore, as a waveform of the stimulation signal, various waveforms suitable for beauty can be applied for the EMS and the RF to be useful for the release of ligaments, the SMAS fascia, and the like, and a so-called drainage mode or the like may be used. But there is no particular limitation, and a conventionally known waveform may be used. Moreover, a larger stimulation may be given using an interference wave formed by combining two or more single waves.

For release of ligaments and the like, it is preferable to use both the EMS and the RF in combination with the suction function, and it is considered that the RF is particularly effective. The RF generates heat in a deeper part of the skin by a radio wave (of high frequency) of about 1 MHz, thermally contracts collagen fibers of the sagging skin by thermal action, and tightens the skin, thereby providing tension. In addition, by combining with the suction function of the suction portion (the pump) 4, the deeper part of the skin can be warmed and loosened, and metabolism can be enhanced.

The EMS can directly apply electrical stimulation to, for example, the facial muscles (white muscles) that move by its own will and deep muscles (red muscles) that are difficult to train, and can train facial expression muscles. By combining with the suction function and the RF wave function (for example, EMS and RF are alternately stimulated), the fascia can be loosened to improve wrinkles and the like, and a face line can be tightened.

The conductive element 34 and the roller 3 are preferably configured using a conductive material so as to generate a stimulation signal and apply the stimulation signal to the facial skin or the like. As the conductive material, examples thereof include a stainless steel (SUS), a silver, a platinum, an aluminum, a duralumin, a copper, and those obtained by subjecting these materials to plating processing such as chromium plating, but are not limited thereto.

(Suction Function)

On the other hand, the suction function of the device 1 according to the present invention is performed by using the opening portion 24 in which the roller 3 and the conductive element 34 are disposed as the suction port, and by operating the pump 4, which is a suction portion that pneumatically communicates with the opening portion 24 and is built in the main body portion 2, to suck external air. In addition, the suction operation of the pump 4 including the output level is adjusted by an operation from the operation panel 5 via the control unit 7 (see FIG. 6).

Figure 10:
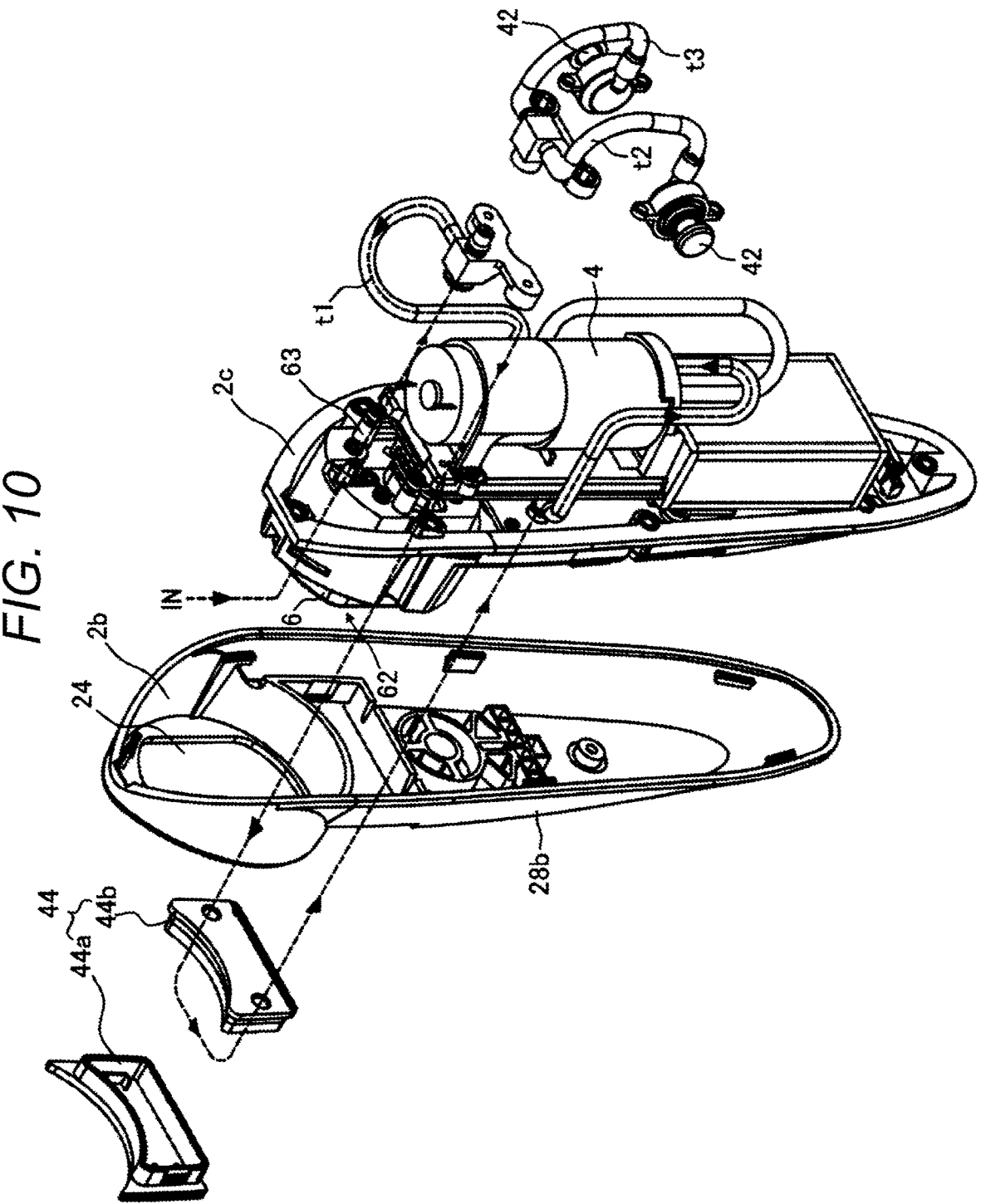
FIG. 10 is an explanatory view illustrating a path of sucked air.

FIG. 10 is an explanatory view illustrating a path of sucked air. In FIG. 10, "IN" indicates suction of air. The pump 4 incorporated in the main body portion 2 is mounted on the component mounting portion 2c combined with the main body lower portion 2b and is fixed inside the main body portion 2. In FIG. 10, the main body upper portion 2a is not placed.

A tube t1 is connected to a cup suction path 63 connected to a suction hole (not illustrated) of the roller cup 6, and pneumatically communicates with the cup suction path 63. Regarding a capacity of the pump 4, the maximum discharge flow rate, the maximum discharge pressure, the maximum vacuum attainment degree, and the like may be appropriately determined in order to suitably maintain a vacuum state during suction.

In the pump 4, an air vent button 42 to be described later is disposed so as to pneumatically communicate with the pump 4 via tubes t2 and t3. Furthermore, a drain tank 44 (also called a drain tank) is detachably attached to the main body portion 2 (the main body lower portion 2b). In FIG. 10, the drain tank 44 is disassembled into a first member 44a appearing outside and a second member 44b hidden inside.

A valve (not illustrated) is attached to the inside of the air vent button 42, and the valve is opened by pressing the air vent button 42. The air vent mechanism included in the device 1 is implemented by pressing the air vent button 42 to open an internal valve so that air is withdrawn from a discharge hole (not illustrated) that pneumatically communicates with the tubes t2 and t3. As described above, in a case where the skin or the like is excessively sucked during execution of the suction function, the sucked air can be discharged to the outside by pressing the air vent button 42 in a state where the pump 4 is stopped.

When the pump 4 is operated in a state where the bottom surface 23 of the main body portion 2 of the device 1 is brought into close contact with the skin or the like, air, a gel (to be described later) (not illustrated) applied to the skin or the like in advance, dirt on the skin or the like, waste products (gel or the like), and the like are sucked through the cup suction path 63 connected to the suction hole (not illustrated) in the opening portion 24 (the opening portion 62 of the roller cup 6) that is a suction port formed in the bottom surface 23. The sucked air, gel, and the like (hereinafter, it may be simply referred to as "air or the like") move in the direction of the pump 4 that is in the upper side and reach the drain tank 44 via the tube t1 around the pump 4 connected to the cup suction path 63.

The drain tank 44 stores the gel or the like that is unnecessary of the air (drain) or the like to be fed. The air from which the gel and the like have been removed is again discharged upward from the drain tank 44, and the vacuum state is maintained.

When the air vent button 42 is pressed while the pump 4 is stopped, a valve in the air vent button 42 is opened (the vacuum state is opened), and air is sucked from the air vent button 42. The sucked air is discharged to the outside from the discharge hole (not illustrated) formed in the opening portion 62 of the roller cup 6 via the tubes t2 and t3 that pneumatically communicate with the air vent button 42.

(II) Method of Using the Device 1

In order to use the device 1 according to the present embodiment, the output level of the EMS mode or the RF mode that is the mode of stimulation function and the suction mode is adjusted by the operation of the operation panel 5, the front side of the bottom surface 23 on which the roller 3 is disposed is brought into contact with the facial skin or the like that is the target to be beauty treated, the device 1 is moved forward or backward along the arrow direction of FIG. 1, and the roller 3 inside the opening portion 24 is rotated and rolled in a state of being in close contact with the facial skin or the like.

By the suction of the pump 4 and the rotation of the roller 3, the facial skin or the like is slowly pulled up into the opening portion 24 that is vacuum. In addition, the rolling roller 3 wraps the pulled up skin or the like, and massages and loosens the ligaments, SMAS fascia, cellulite, and the like existing under the facial skin.

Furthermore, an excretion of waste products can be promoted by a stimulation function based on a stimulation signal such as EMS or RF applied to the fixed conductive element 34 or the roller 3. In this manner, the ligaments present under the facial skin and fat cells entangled with the collagen fibers are massaged and loosened by the massage using the roller 3 and the suction function through the pump 4, the adhesion of the SMAS fascia is peeled off, the metabolism of the fat is increased, and the ligaments and the SMAS fascia obtained by being used in combination with the suction function and the like are efficiently and appropriately released by the electric stimulation function through the application of the stimulation signal (the electric signal) such as EMS and RF. In addition, peeling of adhesion of fascia in the face (the fascia release), elimination of cellulite, and the like can be brought.

Furthermore, before use of the device 1, it is preferable to apply a gel serving as a lubricant or the like to the skin or the like of the user. By applying the gel, the roller 3 of the device 1 easily slides on the skin or the like, and it is possible to prevent an occurrence of redness, internal bleeding, and the like. Moreover, the gel has an effect of enhancing the airtightness of the roller 3 to the roller cup 6 and the skin, and complements the suction function of the device 1. Furthermore, it also serves as a medium for conducting electrical stimulation such as EMS and RF by the stimulation function to the skin or the like sucked into the roller cup 6.

The component constituting the gel is not particularly limited, but a gel containing, using water as a solvent, component such as a glycerin, a BG (butylene glycol), a DPG (a dipropylene glycol), a carbomer, a xanthan gum, an arginine, an alge extract, a ginkgo leaf extract, a grape leaf extract, a rhesus nut extract, a reeds leaf/stem extract, a yerba mate tea leaf extract, a coffee seed extract, a PEG-60 almond fatty acid glyceryl, a cetyl hydroxyethyl cellulose, a methyl paraben, an allantoin, a glycyrrhizic acid 2K, a phenoxyethanol, a potassium hydroxide, a hydrolyzed collagen, a water-soluble collagen, a hypericum erectum extract, an alnica flower extract, a Chinese sweet gum extract, a Mallow extract, an Achillea Millefolium extract, a sage leaf extract, a Calendula officinalis extract, or the like may be used.

(III) Effect of the Present Invention

According to the present invention described above, since the device 1 has a massage function by rolling of the roller 3 disposed in the main body portion 2, a suction function by the suction portion (the pump) 4, and a stimulation function by outputting the stimulation signal by the conductive element 34 fixed to the bottom surface 23 or the roller 3 (the electrical stimulation function by applying the stimulation signal (the electrical signal)), and all these functions can be implemented in combination during use, it is possible to efficiently and reliably release the ligaments and SMAS fascia of the facial skin or the like of the user, and it is possible to efficiently and reliably implement cosmetic treatment of the face such as treatment or care of the face. In addition, according to the present invention, it is possible to easily perform the so-called fascia release for efficiently peeling adhesion of fascia of the facial skin of the user, elimination of cellulite, and the like.

In addition, since the bank-like continuous circumferential protrusion 61 is formed on the peripheral edge of the opening portion 24 for performing suction so as to surround the opening portion 24, it is possible to enhance the confidentiality at the time of suction by the suction portion 4, it is possible to reliably suck the hard and loose facial skin into the opening portion 24, and it is possible to appropriately hold the facial skin that is a region to be treated, and the effect described above is efficiently exhibited.

Furthermore, as described above, the device 1 has a multifunctional structure in which the main body portion 2 has a compact structure in which the suction portion 4 and the fixed conductive element 34 or the roller 3 capable of outputting the stimulation signal to the bottom surface 23 are disposed and integrated, and includes the insertion portion 21 formed of a space into which the hand H of the user can be inserted, and the placement portion 22 capable of placing the palm P of the hand of the user inserted inside the insertion portion 21 on the outer surface, and can be used by being grasped with one hand, and is easy for the user to use even at home.

The present invention is the device 1 that can efficiently and reliably perform massage that is conventionally performed by using fingers or hands or by using a device in which a part to be massaged is only a roller.

In the present invention, in use, the hardened and loosened facial skin (the skin) of the user is sucked and held inside the roller cup 6, and is massaged and loosened by the roller 3, whereby the hardened ligaments can be gradually released. In addition, stimulation is simultaneously applied to the ligaments present under the facial skin sucked into the roller cup 6 by the conductive element 34 and the roller 3 by the EMS or the RF, so that the release of ligaments and the peeling of adhesion of the SMAS fascia (the release of the SMAS fascia) can be efficiently performed.

According to the present invention, it is possible to output (apply) the RF not only to the EMS as the stimulation signal but also to the hard and loose skin sucked into the roller cup 6 and the skin including the fascia. It is difficult to continue the facial massage with the conventional massage method since there is a case where the facial massage is painful only by pushing in a state where the ligaments are hard. On the other hand, in the present invention, as described above, the skin is massaged and loosened with the roller while being sucked into the roller cup 6, and the hardened ligaments are easily and efficiently released by the stimulation signal such as EMS and RF, and the SMAS fascia is also released, so that treatment and care of the face can be easily performed.

Note that the treatment to the face using the suction function needs to be efficiently performed in a short time as much as possible. On the other hand, in the present invention, since the stimulation signal of the EMS or the RF can be emitted from the roller 3 in addition to the fixed conductive element, the treatment efficiency can be improved. In particular, when the stimulation signal is the RF, a heat conduction effect can be expected.

Furthermore, the device 1 of the present invention can efficiently peel off the adhesion of facial fascia (other than SMAS fascia) (fascia release) in addition to release of ligaments and SMAS facial fascia. In so-called myofascial pain syndrome (MPS), no abnormality is observed in the examination, and a place where the pain is felt and a place where the pain occurs (a trigger point) are often separated. In addition, most of such trigger points are considered to be portions where fascia adhere.

In many treatment methods for MPS, pain is removed by fascia release for eliminating adhesion of trigger points. The device 1 according to the present invention can perform processing of stretching the fascia in a state where a constant pressure is applied by the roller 3 through applying a stimulation signal such as EMS or RF in a state where the device 1 is massaged and loosened by the roller 3 while sucking. As a result, it is possible to easily release the facial fascia without pain but with a soft sense for the user by a physiotherapy approach of "peeling while pulling", and it is possible to easily release the adhered fascia, which is also a cause of MPS, in a short time without pain.

Furthermore, the device 1 of the present invention is also useful for elimination of cellulite. In the present invention, the cellulite in the deeper part of the facial skin of the user is massaged and loosened by the roller 3 while subcutaneous fat of the face of the user is sucked into the roller cup 6 during use, whereby the entangled collagen fibers are separated from the cellulite, and the excretion of waste products is promoted by providing a gap in the compressed lymphatic vessel or blood vessel, whereby the cellulite including a size reduction can be eliminated.

In addition, it is possible to enhance a synergistic effect of improving the flow (circulation) of the lymphatic vessel and the blood vessel by electrically stimulating the sucked cellulite by the conductive element 34 and the roller 3.

Although the cellulite causes irregularities on the surface of the facial skin and also affects the appearance of the face, such irregularities can be eliminated by eliminating the cellulite according to the present invention. In addition, the elimination of cellulite generally requires a long period of time, and the cellulite has a property of returning to the original state in a short period of time. However, in a cell light care according to the present invention, the flow (circulation) of lymphatic vessels and blood vessels is also improved as described above, and thus the elimination of cellulite can be performed in a relatively short period of time, and regeneration of cellulite can be prevented.

(IV) Embodiment Modifications

Furthermore, the aspects described above illustrate one aspect of the present invention, and the present invention is not limited to the embodiments described above, and it goes without saying that modifications and improvements having the configuration of the present invention and within a range in which an object and effect can be achieved are included in the contents of the present invention. Moreover, a specific structure, shape, and the like in carrying out the present invention may be other structures, shapes, and the like as long as the object and effect of the present invention can be achieved. The present invention is not limited to the embodiments described above, and modifications and improvements within the scope of achieving the object of the present invention are included in the present invention.

In the embodiment described above, the shape of the roller 3 has a substantially egg shape (a spindle shape as a whole with a large diameter at the central portion) as described above, but as the shape of the roller 3, there is no problem in even adopting a shape other than this, for example, a cylindrical shape, a spherical shape, or the like. Furthermore, the rotation of the roller 3 may not be particularly provided with a driving body as described above, or may be electrically rotated by incorporating the driving body (a motor or the like) (not illustrated) in the main body portion 2 or the like.

Similarly, the conductive element 34 also has one aspect in which the shape obtained by cutting the roller 3 in a direction orthogonal to the rotation shaft 31 is further cut by a plane passing through the rotation shaft 31. However, as long as it can emit a stimulation signal, any shape can be adopted without any problem as long as it can emit a stimulation signal.

Although number of the rollers 3 and the number of the conductive elements 34 are two in each of the embodiments described above, the number of the rollers 3 and the number of the conductive elements 34 are not limited to two, and may be any number of one or more.

In the embodiment described above, it has been assumed that the roller cup 6 is fixed to the device 1, but the roller cup 6 including the conductive element 34 and the roller 3 may be detachable from the device 1 (the main body portion 2).

In the embodiment described above, the shape illustrated in FIG. 1 and the like has been described as an example of the shape of the main body portion 2 of the device 1. However, the main body portion 2 can adopt any shape including, on the outer surface, the insertion portion 21 formed of a space into which the hand H of the user can be inserted, and the placement portion 22 on which the palm P of the hand of the user inserted into the insertion portion 21 can be placed.

Furthermore, although the device 1 of the present invention is a beauty device applicable to the face of the human body, it is not necessary to limit application places to a face of a human body and there is no problem even when the device 1 is applied to other parts of the human body and the like. Furthermore, the device 1 can also be expected to exhibit the effects described above depending on the difference in the degree of the parts to be applied and the skin condition.

In addition, a specific structure, shape, and the like at the time of carrying out the present invention may be other structures and the like as long as the object of the present invention can be achieved.

INDUSTRIAL APPLICABILITY

The present invention can be widely applied in a beauty treatment field, a medical field, a hygiene field, and the like as a means for providing a device useful for beauty treatment of a face by releasing the ligaments (the facial ligaments), the SMAS fascia (the facial fascia), and the like, and has high industrial applicability.

REFERENCE SIGNS LIST

1 Device
2 Main body portion
2a Main body upper portion
2b Main body lower portion
2c Component mounting portion
21 Insertion portion
22 Placement portion
23 Bottom surface
24 Opening portion
25 Battery (rechargeable battery)
26 Finger insertion portion
27 Upper beak portion
27a Upper surface of upper beak portion
27b Lower surface of upper beak portion
28 lower beak portion
28a Upper surface of lower beak portion
28b Lower surface of lower beak portion
29 Insertion port
3 Roller
3k Interposing member
3s Attachment base
31 Rotation shaft
31w Washer
32 Electronic circuit board
33 Stimulation signal generation unit
33E EMS signal generation unit
33R RF signal generation unit
34 Conductive element
34d Support
34k Interposing member
4 Suction portion (pump)
42 Air vent button
44 Drain tank
44a First member
44b Second member
5 Operation panel
51 Power button
52 Suction mode button
53 EMS mode button
54 RF mode button
55 Level raising button
56 Level lowering button
57 Level display lamp
58 Battery lamp
6 Roller cup
61 Circumferential protrusion
62 Opening portion of roller cup
63 Cup suction path
7 Control unit
t1 to t3 Tube
H Hand
P Palm
B Back
F Finger

The invention claimed is:

1. A device applicable to a human face, comprising:
a main body portion including, on an outer surface, an insertion portion having a space into which a hand of a user can be inserted, and a placement portion on which a palm of the hand of the user inserted into the insertion portion can be placed;
a roller disposed inside an opening portion formed in a bottom surface of the main body portion and capable of outputting a stimulation signal;
a conductive element fixedly disposed inside the opening portion and capable of outputting a stimulation signal; and
a suction portion configured to be built in the main body portion, pneumatically communicate with the opening portion, and suck external air from the opening portion,
wherein a bank-like continuous circumferential protrusion is formed on a peripheral edge of the opening portion so as to surround the opening portion, the protrusion having a height from the bottom surface of the main body so that a top thereof is below the bottom surface of the main body so as to be in contact with a facial skin when the device is in use; and
the roller disposed in the opening portion is away from the peripheral edge of the opening portion and is invisible in a side view of the device.

2. The device according to claim 1, wherein the roller is 0.5 millimeters (mm) to 3 mm away from the peripheral edge of the opening portion.

3. The device according to claim 1, wherein
the roller and the conductive element are attached inside a roller cup,
the roller cup is disposed on a bottom surface of the main body portion,
the opening portion formed on the bottom surface includes an opening portion of the roller cup, and
the circumferential protrusion is formed of a peripheral edge of the opening portion of the roller cup.

4. The device according to claim 1, wherein the stimulation signal is at least one selected from a group consisting of electrical muscle stimulation (EMS) and radio frequency (RF).

5. The device according to claim 1, wherein
a side of the main body portion into which a hand of the user is inserted has a bill shape in a side view in which the insertion portion is formed between an upper beak portion and a lower beak portion,
the placement portion serves as an upper surface of the lower beak portion, and
the main body portion is formed with a finger insertion portion that communicates with the insertion portion and includes an opening hole into which a finger of a user can be inserted.

6. The device according to claim 5, wherein a lower surface of the upper beak portion and an upper surface of the lower beak portion have a rounded shape protruding upward.

* * * * *